(12) United States Patent
Guerin et al.

(10) Patent No.: US 11,883,512 B2
(45) Date of Patent: Jan. 30, 2024

(54) ALKALINE COMPOSITION COMPRISING AT LEAST THREE DIFFERENT ALKALINE AGENTS FOR THE TREATMENT OF KERATIN FIBRES, METHODS AND USES

(71) Applicant: L'OREAL, Paris (FR)

(72) Inventors: Frédéric Guerin, Saint Ouen (FR); Géraldine Login, Saint Ouen (FR); Arnaud Hucher, Saint Ouen (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 17/772,481

(22) PCT Filed: Oct. 27, 2020

(86) PCT No.: PCT/EP2020/080193
§ 371 (c)(1),
(2) Date: Apr. 27, 2022

(87) PCT Pub. No.: WO2021/083902
PCT Pub. Date: May 6, 2021

(65) Prior Publication Data
US 2023/0037803 A1 Feb. 9, 2023

(30) Foreign Application Priority Data
Oct. 28, 2019 (FR) .................................. 1912065

(51) Int. Cl.
| | | |
|---|---|---|
| *A61Q 5/10* | (2006.01) | |
| *A61K 8/25* | (2006.01) | |
| *A61K 8/34* | (2006.01) | |
| *A61K 8/41* | (2006.01) | |

(52) U.S. Cl.
CPC ............... *A61K 8/25* (2013.01); *A61K 8/342* (2013.01); *A61K 8/41* (2013.01); *A61Q 5/10* (2013.01); *A61K 2800/4322* (2013.01); *A61K 2800/48* (2013.01)

(58) Field of Classification Search
CPC . A61K 8/25; A61K 8/342; A61K 8/41; A61K 2800/4322; A61K 2800/48; A61K 8/731; A61K 8/8152; A61K 2800/5424; A61K 2800/548; A61K 8/44; A61Q 5/10; A61Q 5/08
USPC .......................................................... 8/405
See application file for complete search history.

(56) References Cited

U.S. PATENT DOCUMENTS

| | | | |
|---|---|---|---|
| 7,766,976 B2 * | 8/2010 | Bureiko | A61K 8/731 8/408 |
| 8,257,447 B2 * | 9/2012 | Legrand | A61K 8/4946 8/606 |
| 8,343,237 B2 * | 1/2013 | Legrand | A61Q 5/065 8/405 |
| 2011/0138545 A1 * | 6/2011 | Legrand | A61Q 5/065 8/408 |
| 2017/0340549 A1 | 11/2017 | Anderheggen et al. | |
| 2017/0340553 A1 | 11/2017 | Anderheggen et al. | |
| 2018/0153780 A1 | 6/2018 | Azizova et al. | |

FOREIGN PATENT DOCUMENTS

| | | | |
|---|---|---|---|
| DE | 102005059647 A1 | 6/2007 | |
| FR | 2 925 305 A1 | 6/2009 | |
| FR | 2 925 317 A1 | 6/2009 | |
| FR | 2 925 318 A1 | 6/2009 | |
| FR | 2925317 A1 * | 6/2009 | ............... A61Q 5/10 |
| WO | WO 2017/207191 A1 * | 12/2017 | ............... A61Q 5/10 |

OTHER PUBLICATIONS

International Search Report and Written Opinion of the International Searching Authority, issued in corresponding International Patent Application No. PCT/EP2020/080193, filed Oct. 27, 2020, 15 pages.

* cited by examiner

*Primary Examiner* — Eisa B Elhilo
(74) *Attorney, Agent, or Firm* — Christensen O'connor Johnson Kindness PLLC

(57) ABSTRACT

The present invention relates to a composition comprising arginine, at least one silicate, at least one alkanolamine, and optionally aqueous ammonia and/or at least one compound which generates aqueous ammonia. The composition further comprises at least one thickening agent chosen from non-associative cellulose polymers, anionic associative polymers, non-ionic associative polymers, and their mixtures. The invention also relates to a method for the treatment of keratin fibres, in particular human keratin fibres, such as the hair, comprising the application of at least one composition according to the invention; and also to the use of the composition according to the invention for the treatment of said keratin fibres, and in particular for the oxidation dyeing and/or the bleaching of the latter.

15 Claims, No Drawings

ALKALINE COMPOSITION COMPRISING AT LEAST THREE DIFFERENT ALKALINE AGENTS FOR THE TREATMENT OF KERATIN FIBRES, METHODS AND USES

The present invention relates to a composition comprising arginine, at least one silicate, at least one alkanolamine, and optionally aqueous ammonia and/or at least one compound which generates aqueous ammonia.

The invention also relates to a method for the treatment of keratin fibres, in particular human keratin fibres, such as the hair, comprising the application of at least one composition according to the invention; and also to the use of the composition according to the invention for the treatment of said keratin fibres, and in particular for the oxidation dyeing and/or the bleaching of the latter.

It is known to employ methods for the oxidation dyeing of the hair in order to modify the colour of natural hairs. These methods generally consist in applying, to the keratin fibres, hair compositions comprising oxidation dyes, in the presence of oxidizing agents.

In order to accelerate the process for the dyeing of the hair, the process is generally carried out in the presence of alkaline agents, and the compositions generally comprised aqueous ammonia and optionally alkanolamines as sole alkaline agents.

Such compositions can also be employed for the bleaching of keratin fibres.

However, these alkaline compositions generally comprise high contents of aqueous ammonia, which gives off a strong odour unpleasant to the users. These compositions can also detrimentally affect the quality and/or the integrity of the keratin fibres.

There thus exists a real need to develop compositions which make it possible to reduce the unpleasant odours during use, to minimize the detrimental changes in the keratin fibres, while maintaining a good level of effectiveness, in particular when they are employed in methods for the dyeing or bleaching of keratin fibres.

This aim is achieved by the present invention, which has in particular as subject-matter a composition comprising:

a) arginine, in a content of greater than or equal to 0.1% by weight, with respect to the total weight of the composition;

b) at least one alkaline agent chosen from silicates;

c) at least one alkanolamine; and e) at least one thickening agent chosen from non-associative cellulose polymers, anionic associative polymers, non-ionic associative polymers, and their mixtures.

It has been found that the use of this composition, in particular during a method for the dyeing (or bleaching) of keratin fibres, did not generate strong odours unpleasant to the user, while making it possible to obtain an intense colouring.

Furthermore, the keratin fibres exhibited good integrity after the treatment.

Other subject-matters, characteristics, aspects and advantages of the invention will become even more clearly apparent on reading the description and the example which follow.

In the present description, and unless otherwise indicated:

the expression "at least one" is equivalent to the expression "one or more" and can be substituted for the latter expression; the expression "between . . . and . . . " is equivalent to the expression "ranging from . . . to . . . " and can be substituted for the latter expression, and implies that the limits are included, the term "keratin fibres", according to the present patent application, preferably denotes human keratin fibres and more particularly the hair, the terms "fatty alcohol" and "fatty acid" according to the present patent application respectively denote saturated or unsaturated and linear or branched alcohols and acids comprising at least 8 carbon atoms, the term "polyoxyalkylenated compound" within the meaning of the present invention is understood to mean a compound comprising several oxyethylene and/or oxypropylene and/or glycerol groups; it preferably being possible for the number of ethylene oxide and/or propylene oxide groups to range from 1 to 100, and for the number of glycerol groups to range from 2 to 30, the term "non-polyoxyalkylenated compound" is understood to mean a compound not comprising several oxyethylene and/or oxypropylene and/or glycerol groups.

The Alkaline Agents

The composition according to the invention comprises a) arginine; b) at least one alkaline agent chosen from silicates; c) at least one alkanolamine; and optionally d) at least one alkaline agent chosen from aqueous ammonia, compounds which generate aqueous ammonia, and their mixtures.

Within the meaning of the invention, all the salts, optical isomers, tautomeric forms and solvates of arginine are suitable for the present invention.

The content of arginine present in the composition is greater than or equal to 0.1% by weight, with respect to the total weight of the composition, Preferably, the arginine content is between 0.5% and 25% by weight, more preferentially between 0.5% and 15% by weight, more preferentially still between 0.6% and 10% by weight, better still between 0.8% and 5% by weight, with respect to the total weight of the composition.

The composition according to the invention additionally comprises at least one alkaline agent b) chosen from silicates.

Preferably, the silicates are chosen from salts of silicic acid, its derivatives, and their mixtures.

In particular, the silicates are chosen from salts of metasilicic acid, its derivatives, and their mixtures.

More preferentially, the silicates are chosen from silicates of alkali metals and/or of alkaline earth metals, in particular from metasilicates of alkali metals and/or of alkaline earth metals, more preferentially still from sodium metasilicate, lithium metasilicate, magnesium metasilicate, calcium metasilicate, potassium metasilicate, and their mixtures.

According to a preferred embodiment of the invention, the composition according to the invention comprises sodium metasilicate.

Preferably, the total content of alkaline agent(s) b) present in the composition according to the invention is between 0.01% and 15% by weight, more preferentially between 0.05% and 10% by weight, more preferentially still between 0.1% and 8% by weight, indeed even between 0.5% and 5% by weight, with respect to the total weight of the composition.

The composition according to the invention additionally comprises at least one alkanolamine c).

The term "alkanolamine" is understood to mean, within the meaning of the invention, an organic amine comprising a primary, secondary or tertiary amine functional group, and one or more linear or branched $C_1$ to $C_8$ alkyl groups carrying one or more hydroxyl radicals.

Alkanolamines, such as monoalkanolamines, dialkanolamines or trialkanolamines, comprising from one to three, identical or different, $C_1$ to $C_4$ hydroxyalkyl radicals are in particular suitable for the implementation of the invention.

Mention may be made, among the alkanolamines, of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethyl)aminomethane, and their mixtures.

Preferably, the composition according to the invention comprises at least one alkanolamine c) chosen from monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethyl)aminomethane, and their mixtures.

Very particularly preferably, the composition according to the invention comprises monoethanolamine as alkanolamine c).

Preferably, the composition according to the invention comprises the alkanolamine(s) c) in a total content ranging from 0.01% to 25% by weight, in particular ranging from 0.1% to 20% by weight, even better still from 0.5% to 15% by weight, preferentially from 1% to 10% by weight, with respect to the total weight of the composition.

The composition according to the invention can additionally comprise at least one alkaline agent d) chosen from aqueous ammonia (or ammonium hydroxide), the compounds which generate aqueous ammonia, and their mixtures.

Within the meaning of the invention, the term "compounds which generate aqueous ammonia" is understood to mean one or more compounds capable of forming, in an aqueous medium, aqueous ammonia.

Preferably, the compounds which generate aqueous ammonia are chosen from ammonium salts, more preferentially from ammonium chloride, ammonium bromide, ammonium iodide, ammonium sulfate, ammonium carbonate, and their mixtures.

More preferentially still, the compound which generates aqueous ammonia is ammonium chloride.

Preferably, the alkaline agent d) is aqueous ammonia (ammonium hydroxide).

When the composition according to the invention comprises at least one alkaline agent d), preferably the total content of alkaline agent(s) d) present in the composition is between 0.01% and 15% by weight, more preferentially between 0.05% and 10% by weight, more preferentially still between 0.1% and 8% by weight, indeed even between 0.2% and 5% by weight, with respect to the total weight of the composition.

Preferably, the composition according to the invention comprises the alkaline agents a), b), c) and optionally d) in a total content between 0.5% and 30% by weight, more preferentially between 1% and 25% by weight and more preferentially still between 3% and 20% by weight, with respect to the total weight of the composition.

The Non-Ionic Surfactants

Preferably, the composition according to the invention additionally comprises at least one non-ionic surfactant.

By way of examples, the non-ionic surfactants can be chosen from alcohols, α-diols and ($C_{1-20}$)alkylphenols, these compounds being (poly)ethoxylated and/or (poly)propoxylated and/or (poly)glycerolated, it being possible for the number of ethylene oxide and/or propylene oxide groups to range from 1 to 150 and it being possible for the number of glycerol groups to range from 2 to 30, these compounds preferably comprising at least one fatty chain comprising from 6 to 40 carbon atoms, in particular from 16 to 30 carbon atoms.

Mention may also be made of condensates of ethylene oxide and of propylene oxide with fatty alcohols; polyethoxylated fatty amides preferably having from 2 to 30 ethylene oxide units, polyglycerolated fatty amides comprising, on average, from 1 to 5, and in particular from 1.5 to 4, glycerol groups; ethoxylated fatty acid esters of sorbitan preferably having from 2 to 40 ethylene oxide units, fatty acid esters of sucrose, polyoxyalkylenated and preferably polyoxyethylenated fatty acid esters having from 2 to 150 mol of ethylene oxide, including oxyethylenated vegetable oils, N-($C_{6-24}$ alkyl)glucamine derivatives, amine oxides, such as ($C_{10-14}$ alkyl)amine oxides or N-($C_{10-14}$ acyl)aminopropylmorpholine oxides.

Mention may also be made of non-ionic surfactants of alkyl (poly)glycoside type, in particular represented by the following general formula:

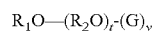

in which:
$R_1$ represents a linear or branched alkyl or alkenyl radical comprising from 6 to 24 carbon atoms, in particular from 8 to 18 carbon atoms, or an alkylphenyl radical, the linear or branched alkyl radical of which comprises from 6 to 24 carbon atoms, in particular from 8 to 18 carbon atoms;

$R_2$ represents an alkylene radical comprising from 2 to 4 carbon atoms,

G represents a sugar unit comprising from 5 to 6 carbon atoms, t denotes a value ranging from 0 to 10, preferably from 0 to 4, v denotes a value ranging from 1 to 15, preferably from 1 to 4.

Preferably, the alkyl (poly)glycoside surfactants are compounds of the formula described above in which:
$R_1$ denotes a saturated or unsaturated and linear or branched alkyl radical comprising from 8 to 18 carbon atoms, $R_2$ represents an alkylene radical comprising from 2 to 4 carbon atoms, t denotes a value ranging from 0 to 3, preferably equal to 0, G denotes glucose, fructose or galactose, preferably glucose, the degree of polymerization, that is to say the value of v, being able to range from 1 to 15, preferably from 1 to 4, the mean degree of polymerization more particularly being between 1 and 2.

The glucoside bonds between the sugar units are generally of 1-6 or 1-4 type and preferably of 1-4 type. Preferably, the alkyl (poly)glycoside surfactant is an alkyl (poly)glucoside surfactant. $C_8/C_{16}$ alkyl (poly)glucosides of 1-4 type, and in particular decyl glucosides and caprylyl/capryl glucosides, are very particularly preferred.

Mention may be made, among the commercial products, of the products sold by Cognis under the Plantaren® (600 CS/U, 1200 and 2000) or Plantacare® (818, 1200 and 2000) names; the products sold by SEPPIC under the names Oramix CG 110 and Oramix® NS 10; the product sold by BASF under the name Lutensol GD 70, or the products sold by Chem Y under the name AG10 LK.

Preferably, use is made of $C_8/C_{16}$ alkyl (poly)glycosides of 1-4 type, in particular as a 53% aqueous solution, such as that sold by Cognis under the reference Plantacare® 818 UP.

Preferentially, the non-ionic surfactant(s) are chosen from ($C_{6-24}$ alkyl) (poly)glycosides and more particularly ($C_{8-18}$ alkyl) (poly)glycosides, polyoxyethylenated $C_8$-$C_{30}$ fatty acid esters of sorbitan, polyoxyethylenated and/or polyoxypropylenated $C_8$-$C_{30}$ fatty alcohols or polyoxyethylenated $C_8$-$C_{30}$ fatty acid esters, these compounds preferably having from 2 to 150 mol of ethylene oxide, and their mixtures.

More preferentially still, the non-ionic surfactant(s) are chosen from polyoxyethylenated $C_8$-$C_{30}$ fatty alcohols or polyoxyethylenated $C_8$-$C_{30}$ fatty acid esters, these compounds preferably having from 2 to 150 mol of ethylene oxide, and their mixtures.

Preferably, when they are present, the composition according to the invention comprises said nonionic surfactant(s) in a total content ranging from 0.01% to 25% by weight, in particular ranging from 0.1% to 20% by weight, even better still from 0.2% to 15% by weight, preferentially from 0.5% to 10% by weight, with respect to the total weight of the composition.

The Fatty Substances

Preferably, the composition according to the invention can additionally comprise at least one fatty substance.

The term "fatty substance" is understood to mean an organic compound which is insoluble in water at ambient temperature (25° C.) and at atmospheric pressure ($1.013 \times 10^5$ Pa), that is to say with a solubility of less than 5% by weight, preferably of less than 1% by weight. They are generally soluble, under the same temperature and pressure conditions, in organic solvents, such as chloroform, ethanol, benzene, liquid petrolatum or decamethylcyclopentasiloxane.

Preferably, the fatty substance(s) of the composition according to the invention are non-silicone fatty substance(s).

The term "non-silicone fatty substance" is understood to mean a fatty substance, the structure of which does not comprise a silicon atom, thus not comprising in particular a siloxane group. They generally exhibit, in their structure, a hydrocarbon chain comprising at least 6 carbon atoms.

The fatty substance(s) of the composition according to the invention are non-polyoxyalkylenated.

The fatty substance(s) which can be used according to the invention can be liquid or non-liquid at ambient temperature (25° C.) and at atmospheric pressure.

The liquid fatty substances which can be used in the invention preferably exhibit a viscosity of less than or equal to 2 Pa·s, better still of less than or equal to 1 Pa·s and even better still of less than or equal to 0.1 Pa·s at a temperature of 25° C. and at a shear rate of 1 $s^{-1}$, measured with a Rheomat RM180 (generally with the spindle 1 or 2).

The liquid fatty substances which can be used according to the invention can in particular be chosen from liquid hydrocarbons, liquid fatty alcohols, liquid fatty esters, liquid fatty acids and the mixtures of these compounds.

The term "liquid hydrocarbon" is understood to mean a hydrocarbon composed solely of carbon and hydrogen atoms, which is liquid at ordinary temperature (25° C.) and at atmospheric pressure (760 mmHg, i.e. $1.013 \times 10^5$ Pa).

More particularly, the liquid hydrocarbons are chosen from:
- linear or branched, optionally cyclic, $C_6$-$C_{16}$ alkanes. Mention may be made, by way of examples, of hexane, undecane, dodecane, tridecane and isoparaffins, such as isohexadecane, isododecane and isodecane.
- linear or branched hydrocarbons of mineral, animal or synthetic origin with more than 16 carbon atoms, such as liquid paraffins and their derivatives, petroleum jelly, liquid petrolatum, polydecenes, hydrogenated polyisobutene, such as that sold under the Parleam® trade name by NOF Corporation, or squalane.

Preferably, the liquid hydrocarbon(s) are chosen from liquid paraffins, isoparaffins, liquid petrolatum, undecane, tridecane, isododecane and their mixtures.

In a very particularly preferred alternative form, the liquid hydrocarbon(s) are chosen from liquid petrolatum, isoparaffins, isododecane and a mixture of undecane and tridecane.

The term "liquid fatty alcohol" is understood to mean a fatty alcohol which is liquid at ordinary temperature (25° C.) and at atmospheric pressure (760 mmHg, i.e. $1.013 \times 10^5$ Pa). Preferably, the liquid fatty alcohols of the invention comprise from 8 to 30 carbon atoms, in particular from 10 to 24 carbon atoms, and they can be saturated or unsaturated.

The saturated liquid fatty alcohols are preferably branched. They can optionally comprise, in their structure, at least one aromatic or non-aromatic ring, preferably acyclic.

More particularly, the saturated liquid fatty alcohols of the invention are chosen from octyldodecanol, 2-decyltetradecanol, isostearyl alcohol or 2-hexyldecanol.

Octyldodecanol and 2-decyltetradecanol are very particularly preferred.

The unsaturated liquid fatty alcohols exhibit, in their structure, at least one double or triple bond, and preferably one or more double bonds. When several double bonds are present, they are preferably 2 or 3 in number and they can be conjugated or non-conjugated.

These unsaturated fatty alcohols can be linear or branched.

They can optionally comprise, in their structure, at least one aromatic or non-aromatic ring. They are preferably acyclic.

More particularly, the unsaturated liquid fatty alcohols which can be used in the invention are chosen from oleyl alcohol, linoleyl alcohol, linolenyl alcohol and undecylenyl alcohol.

Oleyl alcohol is very particularly preferred.

The term "liquid fatty ester" is understood to mean an ester resulting from a fatty acid and/or from a fatty alcohol, which is liquid at ordinary temperature (25° C.) and at atmospheric pressure (760 mmHg, i.e. $1.013 \times 10^5$ Pa).

More particularly, the liquid esters are chosen from esters of saturated or unsaturated and linear or branched $C_1$-$C_{26}$ aliphatic mono- or polyacids, which are optionally hydroxylated, and of saturated or unsaturated and linear or branched $C_1$-$C_{26}$ aliphatic mono- or polyalcohols, the total number of carbon atoms of the esters being greater than or equal to 10.

Preferably, for the esters of monoalcohols, one at least of the alcohol or of the acid from which the esters of the invention result is branched.

Mention may be made, among the monoesters of monoacids and of monoalcohols, of alkyl palmitates, in particular $C_1$-$C_{18}$ alkyl palmitates, in particular ethyl palmitate and isopropyl palmitate, alkyl myristates, in particular $C_1$-$C_{18}$ alkyl myristates, such as isopropyl myristate or ethyl myristate, alkyl stearates, in particular $C_1$-$C_{18}$ alkyl stearates, in particular isocetyl stearate, 2-ethylhexyl isononanoate, isodecyl neopentanoate and isostearyl neopentanoate.

Use may also be made of esters of optionally hydroxylated $C_3$-$C_{22}$ di- or tricarboxylic acids and of $C_1$-$C_{22}$ alcohols and of esters of optionally hydroxylated mono-, di- or tricarboxylic acids and of di-, tri-, tetra- or pentahydroxylated $C_4$-$C_{26}$ non-sugar alcohols.

Mention may in particular be made of diethyl sebacate, diisopropyl sebacate, diisopropyl adipate, di(n-propyl) adipate, dioctyl adipate, diisostearyl adipate, dioctyl maleate, glyceryl undecylenate, octyldodecyl stearoyl stearate, pentaerythrityl monoricinoleate, pentaerythrityl tetraisononanoate, pentaerythrityl tetrapelargonate, pentaerythrityl tetraisostearate, pentaerythrityl tetraoctanoate, propylene glycol dicaprylate, propylene glycol dicaprate, tridecyl erucate, triisopropyl citrate, triisostearyl citrate, glyceryl trilactate, glyceryl trioctanoate, trioctyldodecyl citrate, trioleyl citrate, propylene glycol dioctanoate, neopentyl glycol diheptanoate, diethylene glycol diisononanoate, polyethylene glycol distearates and alkyl malates, in particular ($C_6$-$C_{18}$)alkyl malates, especially bis($C_{12}$-$C_{13}$)alkyl malate. Use is preferentially made, among the abovementioned esters, of ethyl, isopropyl, myristyl, cetyl or stearyl palmitate, 2-ethylhexyl palmitate, 2-octyldecyl palmitate, alkyl myristates, such as isopropyl, butyl, cetyl or 2-octyldodecyl myristate, hexyl stearate, propylene glycol dicaprylate, butyl stearate, isobutyl stearate, dioctyl malate, hexyl laurate, 2-hexyldecyl laurate, isononyl isononanoate, cetyl octanoate and bis($C_{12}$-$C_{13}$)alkyl malate. Use may be made, among liquid fatty esters, of esters and diesters of sugars and of $C_6$-$C_{30}$, preferably $C_{12}$-$C_{22}$, fatty acids.

The term "sugar" is understood to mean oxygen-comprising hydrocarbon compounds which have several alcohol functional groups, with or without aldehyde or ketone functional group, and which comprise at least 4 carbon atoms. These sugars can be monosaccharides, oligosaccharides or polysaccharides.

Preferably, these said sugars are chosen from sucrose, glucose, galactose, ribose, fucose, maltose, fructose, mannose, arabinose, xylose, lactose, and their derivatives, in particular alkylated derivatives, such as methylated derivatives, for example methylglucose.

The esters of sugars and of fatty acids can in particular be chosen from the group consisting of the esters and mixtures of esters of sugars described above and of saturated or unsaturated and linear or branched $C_6$-$C_{30}$, preferably $C_{12}$-$C_{22}$, fatty acids.

If they are unsaturated, these compounds can comprise one to three conjugated or non-conjugated carbon-carbon double bonds.

The esters according to this alternative form can also be chosen from mono-, di-, tri- and tetraesters, polyesters and their mixtures.

These esters can, for example, be oleates, laurates, palmitates, myristates, behenates, cocoates, stearates, linoleates, linolenates, caprates, arachidonates, and their mixtures, such as, in particular, mixed oleate/palmitate, oleate/stearate or palmitate/stearate esters.

More particularly, use is made of sucrose, glucose or methylglucose mono- and diesters and in particular mono- or dioleates, -stearates, -behenates, -oleate/palmitates, -linoleates, -linolenates or -oleate/stearates, or alternatively of methylglucose dioleate (Glucate® DO).

Use may be made, among sugar esters, of pentaerythrityl esters, preferably pentaerythrityl tetraisostearate, pentaerythrityl tetraoctanoate or caprylic and capric acid hexaesters as a mixture with dipentaerythritol.

Use may be made, among natural or synthetic esters of mono-, di- or triacids with glycerol, of vegetable or synthetic oils.

More particularly, said vegetable or synthetic oil(s) are chosen from triglyceride oils of vegetable or synthetic origin, such as liquid fatty acid triglycerides comprising from 6 to 30 carbon atoms, such as heptanoic or octanoic acid triglycerides, or also, for example, sesame oil, soybean oil, coffee oil, safflower oil, borage oil, sunflower oil, olive oil, apricot kernel oil, camellia oil, bambara nut oil, avocado oil, mango oil, rice bran oil, cottonseed oil, rose oil, kiwi seed oil, sea buckthorn pulp oil, bilberry seed oil, poppy seed oil, orange seed oil, sweet almond oil, palm oil, coconut oil, vernonia oil, marjoram oil, baobab oil, rapeseed oil, ximenia oil, pracaxi oil, caprylic/capric acid triglycerides, such as those sold by Stéarineries Dubois or those sold under the names Miglyol® 810, 812 and 818 by Dynamit Nobel, jojoba oil or shea butter oil.

Preferably, use is made, as liquid esters which can be used according to the invention, of triglycerides of vegetable origin, in particular oils chosen from avocado oil, olive oil, camellia oil or apricot kernel oil, and their mixtures, and esters of $C_4$-$C_{22}$ di- or tricarboxylic acids and of $C_1$-$C_{22}$ alcohols, in particular 1,3-propanediol dicaprylate.

The term "fatty acid" is understood to mean a non-salified fatty acid, that is to say that the fatty acid must not be in the generally soluble soap form, that is to say that it must not be salified by a base.

More particularly, the liquid fatty acids which can be used according to the invention are chosen from the acids of formula RCOOH, where R is a saturated or unsaturated and linear or branched radical preferably comprising from 7 to 39 carbon atoms.

Preferably, R is a $C_7$-$C_{29}$ alkyl or $C_7$-$C_{29}$ alkenyl group, better still a $C_{12}$-$C_{24}$ alkyl or $C_{12}$-$C_{24}$ alkenyl group. R can be substituted by one or more hydroxyl groups and/or one or more carboxyl groups.

Preferentially, the liquid fatty acid(s) are chosen from oleic acid, linoleic acid and isostearic acid.

The fatty substance(s) which can be used according to the invention can also be chosen from fatty substances which are non-liquid at ambient temperature (25° C.) and at atmospheric pressure (760 mmHg, i.e. $1.013 \times 10^5$ Pa).

The term "non-liquid fatty substance" is preferably understood to mean a solid compound or a compound exhibiting a viscosity of greater than 2 Pa·s at a temperature of 25° C. and at a shear rate of 1 $s^{-1}$, measured with a Rheomat RM180 (generally with the spindle 1 or 2).

More particularly, the "non-liquid" fatty substances are chosen from fatty alcohols, fatty acid and/or fatty alcohol esters, fatty amines and fatty ethers, which are non-liquid and preferably solid.

More particularly, the non-liquid fatty alcohols which can be used according to the invention are chosen from linear or branched and saturated or unsaturated alcohols comprising from 8 to 30 carbon atoms.

Preferably, mention may be made, for example, of myristyl alcohol, cetyl alcohol, stearyl alcohol, eicosanol, heneicosanol and/or docosanol, and their mixture (in particular cetearyl alcohol). More particularly, eicosanol, heneicosanol and/or docosanol are used.

The non-liquid ester(s) of fatty acids and/or of fatty alcohols which can be used according to the invention are generally chosen from solid esters resulting from $C_9$-$C_{26}$ fatty acids and from $C_9$-$C_{26}$ fatty alcohols.

Preferably, mention may be made, by way of example, of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates, such as cetyl myristate, myristyl myristate or stearyl myristate, and hexyl stearate.

Preferentially, the fatty substance(s) which can be used according to the invention are chosen from hydrocarbons, in particular linear or branched $C_6$-$C_{16}$ alkanes and linear or branched hydrocarbons, of mineral, animal or synthetic origin, of more than 16 carbon atoms, such as liquid paraffins and their derivatives, petroleum jelly, liquid petrolatum; fatty acid esters, in particular oils of vegetable origin and esters of $C_4$-$C_{22}$ di- or tricarboxylic acids and of $C_1$-$C_{22}$ alcohols, these esters being more preferentially chosen from triglycerides of vegetable origin, liquid fatty alcohols, solid fatty alcohols, fatty acids and their mixtures.

Very particularly preferably, the fatty substance(s) are chosen from liquid $C_8$-$C_{30}$ fatty alcohols, solid $C_8$-$C_{30}$ fatty alcohols, and their mixtures.

Preferably, when they are present, the composition according to the invention comprises said fatty substance(s) in a total content ranging from 0.01% to 35% by weight, in particular ranging from 0.1% to 30% by weight, even better still from 0.5% to 20% by weight, preferentially from 1% to 15% by weight, with respect to the total weight of the composition.

The Thickening Agents

The composition according to the invention comprises at least one thickening agent chosen from non-associative cellulose polymers, anionic associative polymers, non-ionic associative polymers, and their mixtures.

The non-associative thickening polymers of the invention can be cellulose polymers not comprising a $C_{10}$-$C_{30}$ fatty chain in their structure.

The term "cellulose" polymer is understood to mean, according to the invention, any polysaccharide compound having, in its structure, sequences of glucose residues joined via β-1,4 bonds; in addition to unsubstituted celluloses, the cellulose derivatives can be anionic, cationic, amphoteric or non-ionic.

Thus, the cellulose polymers which can be used according to the invention can be chosen from unsubstituted celluloses, including under a microcrystalline form, and cellulose ethers.

Among these cellulose polymers, cellulose ethers, cellulose esters and cellulose ether esters are distinguished.

Cellulose esters include inorganic esters of cellulose (cellulose nitrates, sulfates or phosphates, and the like), organic esters of cellulose (cellulose monoacetates, triacetates, amidopropionates, acetate butyrates, acetate propionates or acetate trimellitates, and the like), and mixed organic/inorganic esters of cellulose, such as cellulose acetate butyrate sulfates and acetate propionate sulfates. Mention may be made, among cellulose ether esters, of hydroxypropylmethylcellulose phthalates and ethylcellulose sulfates.

Mention may be made, among non-ionic cellulose ethers without a $C_{10}$-$C_{30}$ fatty chain, i.e. which are "non-associative", of ($C_1$-$C_4$)alkylcelluloses, such as methylcelluloses and ethylcelluloses (for example, Ethocel Standard 100 Premium from Dow Chemical); (poly)hydroxy($C_1$-$C_4$)alkylcelluloses, such as hydroxymethylcelluloses, hydroxyethylcelluloses (for example, Natrosol 250 HHR provided by Aqualon) and hydroxypropylcelluloses (for example, Klucel EF from Aqualon); mixed (poly)hydroxy($C_1$-$C_4$) alkyl/($C_1$-$C_4$)alkylcellulose celluloses, such as hydroxypropyl methylcelluloses (for example, Methocel E4M from Dow Chemical), hydroxyethyl methylcelluloses, hydroxyethyl ethylcelluloses (for example, Bermocoll E 481 FQ from AkzoNobel) and hydroxybutyl methylcelluloses.

The thickening agents can be chosen from anionic associative polymers, non-ionic associative polymers, and their mixtures.

It is recalled that "associative polymers" are polymers which are capable, in an aqueous medium, of reversibly associating with one another or with other molecules.

Their chemical structure more particularly comprises at least one hydrophilic region and at least one hydrophobic region.

The term "hydrophobic region" is understood to mean a radical or polymer having a saturated or unsaturated and linear or branched hydrocarbon chain comprising at least 8 carbon atoms, preferably from 10 to 30 carbon atoms, in particular from 12 to 30 carbon atoms and more preferentially from 18 to 30 carbon atoms.

Preferentially, the hydrocarbon group originates from a monofunctional compound. By way of example, the hydrophobic group can result from a fatty alcohol, such as stearyl alcohol, dodecyl alcohol or decyl alcohol. It can also denote a hydrocarbon polymer, such as, for example, polybutadiene.

Mention may be made, among the associative polymers of anionic type, of:
copolymers comprising, among their monomers, an α,β-monoethylenically unsaturated carboxylic acid and an ester of an α,β-monoethylenically unsaturated carboxylic acid and of an oxyalkylenated fatty alcohol.

Preferentially, these compounds also comprise, as monomer, an ester of an α,β-monoethylenically unsaturated carboxylic acid and of a $C_1$-$C_4$ alcohol.

Mention may be made, as examples of this type of compound, of Aculyn 22® (INCI name: Acrylates/Steareth-20 Methacrylate Copolymer), sold by Rohm and Haas, which is a methacrylic acid/ethyl acrylate/oxyalkylenated stearyl methacrylate terpolymer, and also of Aculyn 88 (INCI name: Acrylates/Steareth-20 Methacrylate Crosspolymer) or Aculyn 28 (INCI name: Acrylates/Beheneth-25 Methacrylate Copolymer), which are also sold by Rohm and Haas.

Mention may be made, among the non-ionic associative polymers which can be used, of:
celluloses or their derivatives, modified by groups comprising at least one fatty chain, such as alkyl, arylalkyl or alkylaryl groups or their mixtures, where the alkyl groups are $C_8$-$C_{30}$ alkyl groups, and in particular:
non-ionic alkylhydroxyethylcelluloses, such as the products Natrosol Plus Grade 330 CS and Polysurf 67 ($C_{16}$ alkyl) sold by Aqualon;
non-ionic nonoxynyl hydroxyethylcelluloses, such as the product Amercell HM-1500 sold by Amerchol;
non-ionic alkylcelluloses, such as the product Bermocoll EHM 100 sold by Berol Nobel;

Preferably, the composition according to the invention comprises said thickening agent(s) in a total content ranging from 0.01% to 10% by weight, in particular ranging from 0.05% to 8% by weight, even better still from 0.1% to 5% by weight, preferentially from 0.2% to 2% by weight, with respect to the total weight of the composition.

Preferably, when they are present, the composition according to the invention comprises said associative polymer(s) in a total content ranging from 0.01% to 10% by weight, in particular ranging from 0.05% to 8% by weight, even better still from 0.1% to 5% by weight, preferentially from 0.2% to 2% by weight, with respect to the total weight of the composition.

Very particularly preferably, the composition according to the invention comprises at least one cellulose polymer, more preferentially still among non-ionic cellulose ethers, even better still among hydroxypropylcelluloses, hydroxypropylmethylcelluloses, and their mixtures.

More preferentially, the composition according to the invention comprises at least one non-associative cellulose polymer and at least one associative cellulose polymer.

Preferably, when they are present, the composition according to the invention comprises said cellulose polymer(s) in a total content ranging from 0.01% to 10% by weight, in particular ranging from 0.05% to 8% by weight, even better still from 0.1% to 5% by weight, preferentially from 0.15% to 2% by weight, with respect to the total weight of the composition.

According to a preferred embodiment of the invention, the thickening agent(s) are chosen from (i) non-ionic cellulose ethers, (ii) copolymers comprising, among their monomers, an α,β-monoethylenically unsaturated carboxylic acid and an ester of an α,β-monoethylenically unsaturated carboxylic acid and of an oxyalkylenated fatty alcohol, (iii) celluloses or their derivatives, modified by groups comprising at least one fatty chain, such as alkyl, arylalkyl or alkylaryl groups or their mixtures, where the alkyl groups are $C_8$-$C_{30}$ alkyl groups, and in particular non-ionic alkylhydroxyethylcelluloses, and (iv) their mixtures; more preferentially from hydroxypropylcelluloses, hydroxypropylmethylcelluloses, cetyl hydroxyethylcelluloses, acrylates/beheneth-25 methacrylate copolymer, cetyl hydroxyethylcellulose, and their mixtures.

According to a preferred embodiment, the composition according to the invention is aqueous.

According to this embodiment, the water content of the composition ranges from 5% to 98% by weight, more preferentially from 15% to 95% by weight, more preferentially still from 25% to 90% by weight and even better still from 30% to 85% by weight, with respect to the total weight of the composition.

The composition according to the invention can optionally comprise, in addition, one or more organic solvents.

Use may in particular be made, as examples of organic solvents, of those which are liquid at 25° C. and $1.013 \times 10^5$ Pa, in particular water-soluble, such as $C_1$-$C_7$ alcohols and in particular $C_1$-$C_7$ aliphatic or aromatic monoalcohols, $C_3$-$C_7$ polyols and $C_3$-$C_7$ polyol ethers, which can thus be employed alone or as a mixture with water. Advantageously, the organic solvent can be chosen from ethanol, isopropanol and their mixtures.

Preferably, the pH of the composition is between 8 and 13, in particular between 9 and 12.5, even better still between 9.5 and 12.5.

The pH of these compositions can be adjusted to the desired value by means of basifying agents or acidifying agents. Use may be made, among the basifying agents, of one or more alkaline agents, such as those described above. Mention may be made, by way of examples, among the acidifying agents, of inorganic or organic acids, such as hydrochloric acid, orthophosphoric acid, carboxylic acids, such as, for example, acetic acid, tartaric acid, citric acid or lactic acid, or sulfonic acids.

The composition according to the invention can additionally contain additives, such as cationic surfactants, amphoteric or zwitterionic surfactants, preservatives, fragrances and/or pigments.

These additives can be present in the composition according to the invention in an amount ranging from 0% to 20% by weight, with respect to the total weight of the composition.

A person skilled in the art will take care to choose these optional additives and their amounts so that they do not harm the properties of the compositions of the present invention.

According to a preferred embodiment of the invention, the composition according to the invention comprises:
a) arginine;
b) sodium metasilicate;
c) monoethanolamine;
d) optionally aqueous ammonia;
e) one or more polyoxyethylenated $C_8$-$C_{30}$ fatty alcohols;
f) one or more fatty substances chosen from liquid $C_8$-$C_{30}$ fatty alcohols, solid $C_8$-$C_{30}$ fatty alcohols, and their mixtures;
g) one or more cellulose thickening polymers; and
h) water.

According to another preferred embodiment of the invention, the composition according to the invention comprises:
a) arginine;
b) sodium metasilicate;
c) monoethanolamine;
d) aqueous ammonia;
e) one or more polyoxyethylenated $C_8$-$C_{30}$ fatty alcohols;
f) one or more fatty substances chosen from liquid $C_8$-$C_{30}$ fatty alcohols, solid $C_8$-$C_{30}$ fatty alcohols, and their mixtures;
g) one or more cellulose thickening polymers; and
h) water.

The composition according to the invention can be provided in the form of a lotion, milk or cream. Preferably, the composition according to the invention is in the form of a cream.

In a specific embodiment, a composition (A) according to the invention is devoid of chemical oxidizing agent and of oxidation dye.

In this embodiment, preferably:
- the content of arginine (a) ranges from 0.5% to 25% by weight, preferentially from 1% to 15% by weight, better still from 1.5% to 10% by weight, indeed even from 2% to 5% by weight, with respect to the total weight of the composition (A)
- the total content of alkaline agent(s) b) chosen from silicates ranges from 0.01% to 15% by weight, more preferentially from 0.1% to 10% by weight, more preferentially still from 1% to 8% by weight, indeed even from 1.5% to 5% by weight, with respect to the total weight of the composition (A)
- the total content of alkanolamine(s) c) ranges from 0.01% to 25% by weight, in particular ranging from 0.1% to 20% by weight, even better still from 0.5% to 15% by weight, preferentially from 1% to 10% by weight, with respect to the total weight of the composition (A)
- the total content of alkaline agent(s) d) chosen from aqueous ammonia and generators of aqueous ammonia, when they are present, ranges from 0.01% to 15% by weight, more preferentially from 0.05% to 10% by weight, more preferentially still from 0.1% to 8% by weight, indeed even from 0.2% to 5% by weight, with respect to the total weight of the composition (A).

In another specific embodiment, a composition according to the invention (M) additionally comprises one or more chemical oxidizing agents and/or one or more oxidation dyes. In particular, the composition (M) can result from the mixing of at least one composition (A) as described above with at least one composition comprising one or more chemical oxidizing agents and/or at least one composition comprising one or more oxidation dyes.

Another subject-matter of the invention is a method for the treatment of keratin fibres, in particular human keratin fibres, such as the hair, comprising the application, to said keratin fibres, of at least one composition according to the invention.

Preferably, the method according to the invention is a method for the oxidation dyeing and/or the bleaching of keratin fibres, in particular human keratin fibres, such as the hair.

More preferably, the method according to the invention is a method for the oxidation dyeing and/or the bleaching of keratin fibres, comprising the application, to said keratin fibres, of a composition (M) as described above, resulting from the extemporaneous mixing of at least one cosmetic composition according to the invention with at least one dyeing composition containing one or more oxidation dyes and/or with at least one oxidizing composition containing one or more chemical oxidizing agents.

In a specific embodiment, the method according to the invention is a method for the oxidation dyeing and/or the bleaching of keratin fibres, comprising the application, to said keratin fibres, of a composition (A) according to the invention as described above devoid of chemical oxidizing agent and of oxidation dye and the application, to said keratin fibres:
- of a dyeing composition (B) containing one or more oxidation dyes, and/or
- of an oxidizing composition (C) containing one or more chemical oxidizing agents, the application of the compositions (A), (B) and/or (C) being carried out simultaneously or sequentially, preferably simultaneously.

When the application of the compositions is carried out simultaneously, the compositions (A), (B) and/or (C) are preferably mixed extemporaneously at the time of use.

The oxidation dye(s) which can be used in said dyeing composition (B) are advantageously chosen from one or more oxidation bases, optionally combined with one or more coupling agents.

By way of example, the oxidation bases are chosen from para-phenylenediamines, bis(phenyl)alkylenediamines, para-aminophenols, ortho-aminophenols and heterocyclic bases, and the corresponding addition salts.

The composition can contain, as oxidation dyes, one or more couplers. Mention may in particular be made, as couplers, of meta-phenylenediamines, meta-aminophenols, meta-diphenols, naphthalene-based coupling agents and heterocyclic coupling agents, and also the corresponding addition salts.

The oxidation base(s) can each advantageously represent from 0.001% to 50% by weight, preferably from 0.005% to 30% by weight, with respect to the total weight of said dyeing composition (B).

The coupler(s), if they are present, can each advantageously represent from 0.001% to 50%, preferably from 0.005% to 30%, by weight, with respect to the total weight of said dyeing composition (B).

The term "chemical oxidizing agent" is understood to mean, within the meaning of the present invention, an oxidizing agent other than atmospheric oxygen.

Preferably, the chemical oxidizing agent(s) (or bleaching agents) which can be used in said aqueous oxidizing composition are chosen from hydrogen peroxide, urea hydrogen peroxide, alkali metal bromates, persalts, such as perborates and persulfates, in particular sodium persulfate, potassium persulfate and ammonium persulfate, peracids and oxidase enzymes (with their optional cofactors), among which may be mentioned peroxidases, 2-electron oxidoreductases, such as uricases, and 4-electron oxygenases, such as laccases, and their mixtures; more preferentially, the chemical oxidizing agent(s) are chosen from hydrogen peroxide, persalts, and their mixtures.

Preferably, the chemical oxidizing agent(s) are present in the aqueous oxidizing composition (C) in a content between 0.1% and 35% by weight, more preferentially between 0.1% and 30% by weight and more preferentially still between 0.5% and 25% by weight, better still between 2% and 15% by weight, with respect to the total weight of the oxidizing composition.

Preferably, the oxidizing composition (C) is aqueous.

Very particularly preferably, the method for the treatment of keratin fibres according to the invention is a method for the oxidation dyeing of keratin fibres comprising the application, to said keratin fibres, of a composition (M) resulting from the extemporaneous mixing (that is a say, mixing immediately before application to the keratin fibres) of at least one composition (A) according to the invention as described above with at least one dyeing composition (B) containing one or more oxidation dyes and with at least one oxidizing composition (C) containing one or more chemical oxidizing agents as described above.

Another subject-matter of the invention is the use of the composition according to the invention for the treatment of keratin fibres, in particular human keratin fibres, such as the hair.

Preferably, the composition according to the invention is used for the oxidation dyeing and/or the bleaching of said keratin fibres.

The examples which follow serve to illustrate the invention without, however, exhibiting a limiting nature.

EXAMPLES

The compositions below according to the present invention were prepared from the ingredients, the contents of which, as percentages by weight of active material, with respect to the total weight of the composition, are shown in the tables below.

TABLE 1

| Ingredients | A1 | A2 |
|---|---|---|
| Arginine | 3 | 3 |
| Monoethanolamine | 5.8 | 5.8 |
| Sodium metasilicate | 2 | 2 |
| Ammonium hydroxide | 2.06 | — |
| Polyquaternium-6 | 2 | 2 |
| Hexadimethrine chloride | 1.2 | 1.2 |
| 2-Oleamido-1,3-octadecanediol | 0.01 | 0.01 |
| EDTA | 0.20 | 0.20 |
| Hydroxypropylmethyl cellulose (HPMC) | 0.20 | 0.20 |
| Cetyl hydroxyethyl cellulose | 0.45 | 0.45 |
| PEG-40 stearate | 1.80 | 1.80 |
| Oleth-30 | 1.50 | 1.50 |
| Oleic acid | 3 | 3 |
| Stearic acid | 0.1 | 0.1 |
| $C_{20}$-$C_{22}$ fatty alcohols | 3 | 3 |
| Stearamide MEA | 4.8 | 4.8 |
| Steareth-2 | 5.50 | 5.50 |
| Water | q.s. 100 | q.s. 100 |

At the moment of use, the compositions A1 and A2 are mixed with 1.5 times their weight of 20 volume oxidizing composition (6 g % am of $H_2O_2$) and ⅓ times their weight of solid particles comprising oxidation dyes.

The compositions below were prepared from the ingredients, the contents of which, as percentages by weight of active material, with respect to the total weight of the composition, are shown in the tables below.

Alkaline Composition 1 According to the Invention

TABLE 2

| Ingredients | Amount |
| --- | --- |
| Arginine | 3 |
| Ammonium hydroxide | 2 |
| Monoethanolamine | 5.8 |
| Sodium metasilicate | 2 |
| Polyquaternium-6 | 2 |
| Hexadimethrine chloride | 1.2 |
| EDTA | 0.2 |
| Hydroxypropylmethyl cellulose (HPMC) | 0.2 |
| Cetyl hydroxyethyl cellulose | 0.45 |
| PEG-40 stearate | 1.8 |
| Oleth-30 | 1.5 |
| Oleic acid | 3 |
| $C_{20}$-$C_{22}$ fatty alcohols | 3 |
| Stearamide MEA | 4.8 |
| Steareth-2 | 5.5 |
| Water | q.s. 100 |

Alkaline Composition 2 According to the Invention

TABLE 3

| Ingredients | Amount |
| --- | --- |
| Arginine | 3 |
| Monoethanolamine | 5.8 |
| Sodium metasilicate | 2 |
| Polyquaternium-6 | 2 |
| Hexadimethrine chloride | 1.2 |
| EDTA | 0.2 |
| Hydroxypropylmethyl cellulose (HPMC) | 1.2 |
| Cetyl hydroxyethyl cellulose | 0.45 |
| PEG-40 stearate | 1.8 |
| Oleth-30 | 1.5 |
| Oleic acid | 3 |
| $C_{20}$-$C_{22}$ fatty alcohols | 3 |
| Stearamide MEA | 4.8 |
| Steareth-2 | 5.5 |
| Water | q.s. 100 |

Oxidizing Composition

TABLE 4

| Ingredients | Amount (g) |
| --- | --- |
| Hydrogen peroxide | 12 |
| Stabilizer, sequestrant | q.s. |
| Phosphoric acid | q.s. pH = 2.2 ± 0.2 |
| Water | q.s. 100 |

Thickening Composition

TABLE 5

| Ingredients | Amount |
| --- | --- |
| Hydrogen peroxide | 12 |
| Cetearyl alcohol | 8 |
| Acrylates/Beheneth-25 Methacrylate copolymer, under the reference Aculyn 28 from Rohm and Haas | 0.4 |
| Ceteareth-33 | 2 |
| Sequestrants, stabilizers | q.s. |
| Phosphoric acid | q.s. pH = 2.2 ± 0.2 |
| Water | q.s. 100 |

Examples of Dyeing Compositions

TABLE 6

| Ingredients | Amount |
| --- | --- |
| Microcrystalline cellulose | 54.4 |
| Lactose | 14.6 |
| PVP | 4.6 |
| Magnesium stearate | 1.94 |
| Silica | 1.0 |
| Toluene-2,5-diamine sulfate | 19.4 |
| Sodium sulfite | 1.0 |
| Water | 0.2 |
| Hydroxypropyl methylcellulose | 1.46 |
| Hydroxypropylcellulose | 0.29 |
| Talc | 0.44 |
| Caprylic/capric triglyceride | 0.15 |
| Pigments | 0.51 |
| Alumina | 0.01 |

TABLE 7

| Ingredients | Amount |
| --- | --- |
| Microcrystalline cellulose | 77.2 |
| Lactose | 14.6 |
| PVP | 0.1 |
| Magnesium stearate | 1 |
| Silica | 0.54 |
| Resorcinol | 0.85 |
| Hydroxypropyl methylcellulose | 1.45 |
| Hydroxypropylcellulose | 0.30 |
| Talc | 0.4 |
| Caprylic/capric triglyceride | 0.15 |
| Pigments | 0.5 |
| Alumina | 0.01 |
| VP/VA copolymer | 2.9 |

TABLE 8

| Ingredients | Amount |
| --- | --- |
| Microcrystalline cellulose | 63.5 |
| Lactose | 9.7 |
| PVP | 0.1 |
| Magnesium stearate | 1 |
| Silica | 0.5 |
| Resorcinol | 16.5 |
| Ascorbic acid | 2.9 |
| Hydroxypropyl methylcellulose | 1.5 |
| Hydroxypropylcellulose | 0.3 |
| Talc | 0.44 |
| Caprylic/capric triglyceride | 0.15 |
| Pigments | 0.5 |
| Alumina | 0.01 |
| VP/VA copolymer | 2.9 |

TABLE 9

| Ingredients | Amount |
| --- | --- |
| Microcrystalline cellulose | 76.2 |
| Lactose | 15.5 |
| PVP | 0.5 |
| Magnesium stearate | 1.0 |
| Silica | 1.0 |
| 2,4-Diaminophenoxyethanol hydrochloride | 1.0 |
| Sodium metabisulfite | 1.94 |
| Water | 0.02 |
| Hydroxypropyl methylcellulose | 1.45 |
| Hydroxypropylcellulose | 0.29 |

TABLE 9-continued

| Ingredients | Amount |
| --- | --- |
| Talc | 0.44 |
| Caprylic/capric triglyceride | 0.15 |
| Pigments | 0.5 |
| Alumina | 0.01 |

TABLE 10

| Ingredients | Amount |
| --- | --- |
| Microcrystalline cellulose | 69.4 |
| Lactose | 11.6 |
| PVP | 2.8 |
| Magnesium stearate | 1.0 |
| Silica | 0.5 |
| m-Aminophenol | 7.8 |
| Sodium metabisulfite | 3.9 |
| Water | 0.15 |
| Hydroxypropyl methylcellulose | 1.46 |
| Hydroxypropylcellulose | 0.29 |
| Talc | 0.44 |
| Caprylic/capric triglyceride | 0.15 |
| Pigments | 0.5 |
| Alumina | 0.01 |

Method for Dyeing Keratin Fibres

A composition (M) for the dyeing of keratin fibres is prepared in a bowl according to the following stages:

(1) 6 g of dyeing composition according to Table 6 above, 3.48 g of dyeing composition according Table 8 above, 1.32 g of dyeing composition according to Table 7 above, 1.26 g of dyeing composition according to Table 9 above and 0.84 g of dyeing composition according to Table 10 above are mixed with 12 g of oxidizing composition according to Table 4 above and 36 g of water stabilized and adjusted to pH 2,2; then, after at least 30 seconds, (2) the mixture obtained in stage (1) is mixed with 24 g of thickening composition according to Table 5 above, 28.8 g of alkaline composition 1 (invention) according to Table 2 above and 19.2 g of alkaline composition 2 (invention) according to Table 3 above.

A homogeneous aqueous composition (M), where the dyeing compositions have dispersed in the aqueous composition (M), is thus obtained.

The composition (M) obtained is subsequently applied to locks of natural Caucasian hair comprising 90% white hairs (locks of NG hair) in a proportion of 10 g of composition (M) per 1 g of hair. After a leave-in time of 30 minutes at 27° C., the locks are rinsed, washed with a standard shampoo, rinsed again and then dried.

Results for the Dyeing:

The colorimetric data for each of the locks are subsequently measured in the CIELab system with a Data Color SF600X spectrophotometer (illuminant D65, angle 10° and specular component included). In this L* a* b* system, L* represents the lightness, a* indicates the green/red colour axis and b* indicates the blue/yellow colour axis. The higher the value of L, the lighter or less intense the colour. Conversely, the lower the value of L*, the darker or more intense the colour. The higher the value of a*, the redder the shade, and the higher the value of b*, the yellower the shade.

The colour build-up on hair thus corresponds to the variation in colouring between the locks of dyed NG hair and the locks of non-dyed (i.e. untreated) NG hair, which is measured by ΔE according to the following equation:

$$\Delta E = \sqrt{(L^*-L_0^*)^2 + (a^*-a_0^*)^2 + (b^*-b_0^*)^2}$$

In this equation, L*, a* and b* represent the values measured after dyeing of the locks of NG hair, and $L_0^*$, $a_0^*$ and $b_0^*$ represent the values measured for the locks of untreated NG hair. The higher the ΔE value, the better the build-up of the colouring.

The results are collated in the table below:

TABLE 11

| | L* | a* | b* | ΔE |
| --- | --- | --- | --- | --- |
| Lock of untreated NG hair | 57.78 | 1.40 | 13.97 | — |
| Lock of treated NG hair | 23.57 | 2.39 | 5.25 | 35.32 |

It is apparent from the results of the table that the keratin fibres treated with the composition (M) prepared by means of the cosmetic composition according to the invention are dyed intensely and with a good colour build-up.

It has also been found that the composition (M) is easy to apply and to spread over the locks of hair, in particular without running.

Method for Bleaching Keratin Fibres

A composition (N) for the bleaching of keratin fibres is prepared in a bowl by mixing 12 g of oxidizing composition according to Table 4 above with 36 g of water stabilized and adjusted to pH 2.2, then with 24 g of thickening composition according to Table 5 above and 48 g of alkaline composition 1 (invention) according to Table 2 above.

A homogeneous aqueous composition (N) is thus obtained.

The composition (N) obtained is subsequently applied to locks of natural Caucasian hair with a height of tone 4 (HT4) in a proportion of 10 g of composition (N) per 1 g of hair. After a leave-in time of 30 minutes at 27° C., the locks are rinsed, washed with a standard shampoo, rinsed again and then dried.

Results for the bleaching:

The colour of the locks was evaluated in the CIE L* a* b* system by means of a Data Color SF600X spectrophotometer (illuminant D65, angle 10° and specular component included). In this L* a* b* system, the three parameters respectively denote the intensity of the colour (L*), the green/red colour axis (a*) and the blue/yellow colour axis (b*).

The higher the value of L*, the more the locks are bleached. The higher the value of a*, the redder the shade, and the higher the value of b*, the yellower the shade. The effectiveness of the bleaching is evaluated by the variation in the colour of the locks before and after treatment with the composition (N), and measured by (ΔE*) according to the following equation:

$$\Delta E = \sqrt{(L^*-L_0^*)^2 + (a^*-a_0^*)^2 + (b^*-b_0^*)^2}$$

In this equation, L*, a* and b* represent the values measured on the locks of HT4 hair treated with the composition (N), and $L_0^*$, $a_0^*$ and $b_0^*$ represent the values measured on the locks of untreated HT4 hair.

The greater the value of ΔE*, the greater the difference in colour of the lock before and after treatment, which shows a more intensive bleaching.

The results are collated in the table below:

TABLE 12

|  | L* | a* | b* | ΔE |
|---|---|---|---|---|
| Lock of untreated HT4 hair | 21.33 | 2.84 | 3.24 | — |
| Lock of treated HT4 hair | 26.22 | 6.91 | 9.43 | 8.88 |

It is apparent from the results of the table above that the keratin fibres treated with the composition (N) prepared by means of the cosmetic composition according to the invention are significantly bleached ($L^*>L_0$ and high $\Delta E$).

It has also been found that the composition (N) is easy to apply and to spread over the locks of hair, in particular without running.

The invention claimed is:

1. A composition comprising:
   a) arginine, in a content of greater than or equal to 0.1% by weight, with respect to the total weight of the composition;
   b) at least one alkaline agent chosen from silicates;
   c) at least one alkanolamine; and
   e) at least one thickening agent chosen from non-associative cellulose polymers, anionic associative polymers, non-ionic associative polymers, and their mixtures
   wherein the composition is free of any chemical oxidizing agent; and
   the pH of the composition ranges from 9.5 to 12.5.

2. The composition according to claim 1, characterized in that the arginine content is between 0.5% and 25% by weight, with respect to the total weight of the composition.

3. The composition according to claim 1, characterized in that the silicate(s) are chosen from sodium metasilicate, lithium metasilicate, magnesium metasilicate, calcium metasilicate, potassium metasilicate, and their mixtures.

4. The composition according to claim 1, characterized in that the total content of alkaline agent(s) b) is between 0.01% and 15% by weight, with respect to the total weight of the composition.

5. The composition according to claim 1, characterized in that the alkanolamine(s) c) are chosen from monoethanolamine, diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethyl)aminomethane, and their mixtures.

6. The composition according to claim 1, characterized in that the total content of alkanolamine(s) c) is between 0.01% and 25% by weight, with respect to the total weight of the composition.

7. The composition according to claim 1, characterized in that it additionally comprises at least one alkaline agent d) chosen from aqueous ammonia (ammonium hydroxide), the compounds which generate aqueous ammonia, their mixtures.

8. The composition according to claim 7, characterized in that the compounds which generate aqueous ammonia are chosen from ammonium salts.

9. The composition according to claim 1, characterized in that the total content of alkaline agents a), b), c) and optionally d) is between 0.5% and 30% by weight, with respect to the total weight of the composition.

10. The composition according to claim 1, characterized in that it additionally comprises at least one non-ionic surfactant chosen from polyoxyethylenated $C_8$-$C_{30}$ fatty alcohols, polyoxyethylenated $C_8$-$C_{30}$ fatty acid esters, and their mixtures.

11. The composition according to claim 1, characterized in that it additionally comprises at least one fatty substance chosen from liquid $C_8$-$C_{30}$ fatty alcohols, solid $C_8$-$C_{30}$ fatty alcohols, and their mixtures.

12. The composition according to claim 1, characterized in that the thickening agent(s) are chosen from (i) non-ionic cellulose ethers, (ii) copolymers comprising, among their monomers, an α,β-monoethylenically unsaturated carboxylic acid and an ester of an α,β-monoethylenically unsaturated carboxylic acid and of an oxyalkylenated fatty alcohol, (iii) celluloses or their derivatives, modified by groups comprising at least one fatty chain, and (iv) their mixtures.

13. A method for the treatment of keratin fibres, in comprising the application, to said keratin fibres, of at least one composition according to claim 1.

14. The method according to claim 13 for the oxidation dyeing and/or the bleaching of keratin fibres, characterized in that it comprises the application, to said keratin fibres, of a composition (M) resulting from the extemporaneous mixing of the at least one composition according to claim 13 with at least one dyeing composition containing one or more oxidation dyes, and/or with at least one oxidizing composition containing one or more chemical oxidizing agents.

15. The composition according to claim 1, characterized in that the arginine content is between 0.8% and 5% by weight, with respect to the total weight of the composition.

* * * * *